United States Patent
Antons et al.

[11] Patent Number: 5,869,735
[45] Date of Patent: Feb. 9, 1999

[54] PROCESS FOR THE PREPARATION OF ALKYL ARYL ETHERS CONTAINING CARBOXYL GROUPS

[75] Inventors: Stefan Antons, Leverkusen; Erich Hammerschmidt, Bergisch Gladbach; Heinz Ulrich Blank, Odenthal; Helmut Fiege; Heinz-Gerd Hartges, both of Leverkusen, all of Germany

[73] Assignee: Bayer Aktiengesellschaft, Leverkusen, Germany

[21] Appl. No.: 729,461

[22] Filed: Oct. 11, 1996

[30] Foreign Application Priority Data

Oct. 20, 1995 [DE] Germany .................. 195 39 073.3

[51] Int. Cl.$^6$ ................................... C07C 69/76
[52] U.S. Cl. .................... 560/61; 562/471; 562/856
[58] Field of Search ............... 560/61; 582/471, 582/856

[56] References Cited

U.S. PATENT DOCUMENTS 2,511,231  6/1950  Weissberger et al. .
2,728,658  12/1955 McCrossen et al. .
4,681,941  7/1987  Adaway .
5,262,292  11/1993 Krishnamurthy et al. .

FOREIGN PATENT DOCUMENTS

| 0115007 | 8/1984 | European Pat. Off. . |
| 160414 | 7/1983 | Germany . |
| 261277 | 10/1986 | Germany . |
| 261277 | 10/1988 | Germany . |
| 59-130834 | 12/1983 | Japan . |
| 0204745 | 3/1984 | Japan . |

*Primary Examiner*—Paul J. Killos
*Attorney, Agent, or Firm*—Sprung Kramer Schaefer & Briscoe

[57] ABSTRACT

Process for the preparation of alkyl aryl ethers containing carboxyl groups which are suitable for the preparation of colour film couplers, or derivatives thereof, by reaction of aromatic alcohols with alkyl halides containing carboxyl groups or derivatives thereof and basic alkali metal or alkaline earth metal compounds, characterized in that the reaction is carried out in the melt of the aromatic alcohol.

11 Claims, No Drawings

PROCESS FOR THE PREPARATION OF ALKYL ARYL ETHERS CONTAINING CARBOXYL GROUPS

The invention relates to a process for the preparation of alkyl aryl ethers containing carboxyl groups by a specific reaction of aromatic alcohols with alkyl halides containing carboxyl groups and basic alkali metal or alkaline earth metal compounds, and to their use for the preparation of colour film couplers.

In the literature, the preparation of alkyl phenyl ethers containing carboxyl groups from phenolates and alkyl halides containing carboxyl groups has already been realized in various ways. In U.S. Pat. No. 2,511,231 and U.S. Pat. No. 2,728,658, however, the reaction of 2,4-di-tert-pentylphenol with alkyl halides containing carboxyl groups, such as chloroacetic acid or α-bromo-n-butyric acid, in aqueous or aqueous-alcoholic alkali leads to low yields and high contents of by-products. Isolation of the desired ether from the reaction mixtures obtained in this reaction is very expensive. Thus, for example, the removal, proposed in DD-A-261 277, of unreacted residual phenol as a coupling product with a diazonium salt causes additional process steps. To avoid the by-products caused in part by the aqueous-alkaline sodium hydroxide solution, DD 160 414 has proposed reaction with alkali metal hydroxide in an inert aprotic solvent. However, additional solvents are employed in this process, and must be worked up separately, and if necessary disposed of, after the reaction and thus additionally necessitate expensive and troublesome process steps.

The object of the present invention was to provide an improved process for the preparation of alkyl aryl ethers containing carboxyl groups in which the formation of by-products is extremely low and in which the use of additional solvents can be avoided to the greatest extent.

A process has now been found for the preparation of alkyl phenyl ethers containing carboxyl groups or derivatives thereof by reaction of aromatic alcohols with alkyl halides containing carboxyl groups or derivatives thereof and basic alkali metal or alkaline earth metal compounds, which is characterized in that the reaction is carried out in the melt of the aromatic alcohol.

Preferred basic alkali metal or alkaline earth metal compounds are those which are capable of reacting with the aromatic alcohols to form an aromatic alcoholate and water or an aliphatic $C_1$–$C_4$-alcohol.

Particularly preferred basic alkali metal or alkaline earth metal compounds are inorganic alkali metal compounds, such as NaOH, $Na_2CO_3$, $NaHCO_3$, $K_2CO_3$, $Li_2CO_3$, KOH or $KHCO_3$, and aliphatic $C_1$–$C_4$-alkyl alcoholates of lithium, sodium or potassium, in particular of sodium, or mixtures thereof. The basic alkali metal or alkaline earth metal compounds can be employed without solvents or suspending agents or with water or aliphatic $C_1$–$C_4$ alcohols as solvents or suspending agents. If no solvent or suspending agent is used, the alkali metal or alkaline earth metal compound is preferably employed as a solid. The inorganic alkali metal compounds are preferably employed in solid form or, in particular, in the form of their aqueous suspensions or solutions, the latter being preferred and in general being 5 to 70% strength by weight, preferably saturated.

The alkali metal alcoholates, in particular alkali metal methanolate or ethanolate, are preferably employed in solutions of the alcohol on which the alcoholate is based. Preferably, these solutions are 5 to 70% strength by weight, preferably saturated.

The process according to the invention is preferably carried out at or above the melting point of the aromatic alcohol employed under normal pressure, particularly preferably at a temperature of 50° to 200° C., in particular at 80° C. to 150° C. The reaction is in general carried out under normal pressure, but it can also be carried out under reduced pressure, in particular under 20 to 700 mbar, or under increased pressure, in particular under 1 to 10 bar.

The reaction is especially preferably carried out at temperatures which are above the boiling point, under the given pressure, of the water or alcohol of reaction formed during formation of the aromatic alcoholate and of the solvent or suspending agent used, where appropriate, for the basic alkali metal or alkaline earth metal compound.

The water of reaction preferably formed during formation of the aromatic alcoholate or the alcohol of reaction formed are particularly preferably removed by distillation, preferably during the reaction, together with the aliphatic $C_1$–$C_4$-alcohol content or water content of the solvent or suspending agent used, where appropriate, for the basic alkali metal or alkaline earth metal compound. When the reaction has ended, the content of water and aliphatic $C_1$–$C_4$-alcohols in the reaction mixture is preferably less than or equal to 1% by weight.

Derivatives of alkyl aryl ethers containing carboxyl groups are preferably understood as meaning salts, in particular alkali metal salts of sodium, lithium or potassium, or esters, in particular $C_1$–$C_4$-alkyl esters, such as the methyl, ethyl, n-propyl, n-butyl and the branched alkyl esters.

Derivatives of alkyl halides containing carboxyl groups are understood as meaning, in particular, alkali metal salts of sodium, lithium or potassium or esters, in particular $C_1$–$C_4$-alkyl esters.

The preferred derivatives of the alkyl aryl ethers containing carboxyl groups are particularly preferably prepared using the preferred derivatives of the alkyl halides containing carboxyl groups.

In the case where the alkyl halide containing carboxyl groups is to be employed in the form of the free acid, the amount of alkali metal or alkaline earth metal compound is expediently increased by the amount necessary to neutralize the acid to give the carboxylate.

The molar ratios of the reactants in the reaction by the process according to the invention can in general be varied widely. The molar ratio of the aromatic alcohol to the basic alkali metal or alkaline earth metal compound is preferably chosen such that complete formation of the alcoholate of the aromatic alcohol is possible. The ratio is preferably 1:0.9 to 0.9:1 per aromatic hydroxyl group to be etherified. It can of course also be varied beyond this range. The molar ratio of aromatic alcohol and alkyl halide is preferably 1:1 to 1:1.5, in particular 1:1 to 1:1.1 per aromatic hydroxyl group to be etherified. Here also, the ratio can of course be varied more widely.

The process according to the invention is preferably carried out by adding the basic alkali metal or alkaline earth metal compound and the alkyl halide containing carboxyl groups or derivatives thereof to the melt of the aromatic alcohol by means of separate feed lines or metering devices. The two components can be added here in succession or simultaneously.

In a particularly preferred embodiment of the process according to the invention, the alkyl halide containing carboxyl groups or derivatives thereof is added entirely before, partly before or simultaneously with the basic alkali metal or alkaline earth metal compound.

Simultaneous addition is especially preferred.

In the case of simultaneous addition, it is entirely possible for variations in the addition from the desired stoichiometric 1:1 ratio of the two components to occur during the addition without this being detrimental to the understanding of a simultaneous addition as is understood in the context of this Application. Deviations from the stoichiometric 1:1 ratio of 1:1.05 to 1.05:1 during the addition are entirely normal here. Any excesses of one component are preferably added afterwards in the case of simultaneous addition.

Preferred aromatic alcohols are phenols and naphthols, which are optionally further substituted.

Optionally substituted phenol is particularly preferred.

The process according to the invention is particularly suitable for the preparation of alkyl phenyl ethers containing carboxyl groups, of the formula (I)

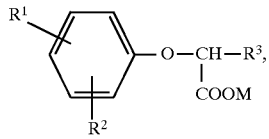

employing phenols of the formula (II)

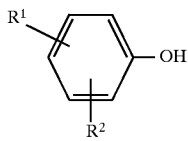

and alkyl halides containing carboxyl groups, of the formula (III)

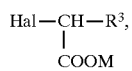

wherein $R^1$ and $R^2$ independently of one another represent hydrogen, straight-chain or branched $C_1$–$C_8$-alkyl, in particular methyl, ethyl, n-propyl, isopropyl, n-butyl, sec-butyl, tert-butyl, n-pentyl or tert-pentyl, $C_5$–$C_8$-cycloalkyl, in particular cyclohexyl, $C_6$–$C_{10}$-aryl-$C_1$–$C_4$-alkyl, in particular benzyl or ethylphenyl, $C_6$–$C_{10}$-aryl, in particular phenyl, hydroxyl, $C_1$–$C_4$-alkoxy, $C_6$–$C_{10}$-aryloxy or halogen, in particular Cl, Br or I, $R^3$ represents hydrogen, straight-chain or branched $C_1$–$C_8$-alkyl, in particular methyl, ethyl, n-propyl, isopropyl or n-butyl, $C_5$–$C_8$-cycloalkyl, in particular cyclopentyl or cyclohexyl, $C_6$–$C_{10}$-aryl-$C_1$–$C_8$-alkyl, in particular benzyl or ethylphenyl, or COOM, wherein M denotes Na, Li, K or $C_1$–$C_4$-alkyl, M denotes Na, Li, K or $C_1$–$C_4$-alkyl and Hal represents Cl, Br, F or I, in particular Br.

Phenols of the general formula (II) which can be employed for the process according to the invention are, for example: 2-tert-butylphenol, 4-tert-butylphenol, 2,4-di-tert-butylphenol, 2-tert-pentylphenol, 4-tert-pentylphenol, 2,4-di-tert-pentylphenol, 2-tert-hexylphenol, 4-tert-hexylphenol, 2,4-di-tert-hexylphenol, 2-chloro-4-tert-amylphenol and 2-tert-butyl-hydroquinone.

Alkyl halides which contain carboxyl groups, of the general formula (III), and can be employed for the process according to the invention are, for example, methyl chloroacetate, ethyl chloroacetate, methyl bromoacetate, ethyl α-bromopropionate, ethyl β-bromopropionate, ethyl α-bromobutyrate, ethyl α-bromoisobutyrate, ethyl γ-bromobutyrate and ethyl α-bromoisobutyrate.

For preparation of enantiomeric alkyl aryl ethers containing carboxyl groups or derivatives thereof, it may also be advantageous for the corresponding alkyl halides containing carboxyl groups or their derivatives already to be employed in the enantiomeric form.

Alkyl aryl ethers containing carboxyl groups can be prepared not only from the salts of the carboxylic acid alkyl halides, but also from their esters. The hydrolysis is preferably carried out after the reaction.

The alkali metal or alkaline earth metal halides present after the reaction has ended are preferably washed out of the resulting product mixture with the required amount of water, after the reaction temperature has been reduced. In the case where an alkyl aryl ether containing carboxylic acid groups is to be isolated in the form of its free acid, an acid, preferably an aqueous mineral acid, such as, for example, HCl, $H_2SO_4$ and the like, is preferably employed for the washing. The compounds prepared by the process according to the invention are of very high purity and are obtained in very good yields, preferably >95% of theory. The advantage of the process according to the invention furthermore lies in the fact that an additional solvent can be omitted during the reaction.

If alkyl halides containing ester groups are used, partial or complete transesterification can take place, for example by using an alcoholic alcoholate solution or suspension of an alcohol which differs from that on which the ester group is based.

It is preferable for the alkyl aryl ethers containing carboxyl groups which are obtainable in the process according to the invention or derivatives thereof, in particular alkali metal derivatives thereof or $C_1$–$C_4$-alkyl esters thereof, to be converted into their acid chlorides, preferably by reaction with thionylchloride or $COCl_2$ or other chlorinating agents. These products are particularly preferably employed in the preparation of colour film couplers. The alkyl aryl ethers containing carboxyl groups which are obtained by the process according to the invention, or derivatives thereof, can be used, for example, for the preparation of colour film couplers, such as are described in U.S. Pat. No. 2,511,231 or U.S. Pat. No. 5,262,292, or as intermediate products for plant protection agents or for pharmaceuticals.

EXAMPLES

Abbreviations: Me=methyl, Et=ethyl

Example 1

Preparation of a 2-(2,4-di-tert-butylphenoxy)caproic acid ester mixture 206 g (1 mol) of 2,4-di-tert-butylphenol were melted and heated to 140° C. under nitrogen. 185 g (1.03 mol) of a 30% strength NaOMe solution in MeOH and 245 g (1.1 mol) of ethyl 2-bromocaproate were metered in simultaneously in the course of 1 hour. During the addition, a mixture of MeOH and EtOH was distilled off. After the addition, the reaction was ended. The mixture was cooled to 90° C. and 250 ml of water were added. After separation of the phases and washing with 200 ml of water, 350 g of a viscous yellow oil of the following composition (0.8% of ethyl bromocaproate, 0.7% of residual phenol, 68% of ethyl 2-(2,4-di-tert-butylphenoxy)caproate and 29% of methyl 2-(2,4-di-tert-butylphenoxy)caproate) remained. This corresponds to a yield of 98.8% of theory, based on the phenol employed.

Example 2

Preparation of ethyl 2-(2,4-di-tert-butylphenoxy) caproate 206 g (1 mol) of 2,4-di-tert-butylphenol were melted and heated to 140° C. under nitrogen. 185 g (1.03 mol) of a 30% strength NaOMe solution in MeOH and 245 g (1.1 mol) of ethyl 2-bromocaproate were metered in simultaneously in the course of 1 hour. During the addition, a mixture of MeOH and EtOH was distilled off. After the addition, the reaction to give the ester mixture was complete. The mixture was cooled to 80° C., 20 g of NaOMe solution were added and 750 ml of ethanol were then added in the course of 4 hours. A methanol/ethanol mixture distilled off at an overhead temperature of initially 74° to 76° C. At the end, the temperature was increased to 90° C. and pure ethanol distilled over at 78° to 79° C. For isolation, 250 ml of water were added. After separation of the phases and renewed washing with 200 ml of water, 351 g of a viscous yellow oil of the following composition (0.3% of ethyl bromocaproate, 0.7 g of residual phenol, 98% of ethyl 2-(2,4-di-tert-butylphenoxy)caproate and 0.3% of methyl 2-(2,4-ditert-butylphenoxy)caproate, remained. This corresponds to a yield of 98.8% of theory, based on the phenol employed.

Example 3

Preparation of ethyl 2-(2,4-di-tert-butylphenoxy) caproate 206 g (1 mol) of 2,4-di-tert-butylphenol were melted and heated to 140° C. under nitrogen. 234 g (1.03 mol) of a 30% strength NaOEt solution in EtOH and 245 g (1.1 mol) of ethyl 2-bromocaproate were metered in simultaneously in the course of 1 hour. During the addition, EtOH was distilled off. After the addition, the reaction was ended. The mixture was cooled to 90° C. and 250 ml of water were added. After separation of the phases and washing with 200 ml of water, 347 g of a viscous yellow oil of the following composition (0.3% of ethyl bromocaproate, 0.5% of residual phenol and 98% of ethyl 2-(2,4-di-tert-butylphenoxy)caproate, remained. This corresponds to a yield of 98% of theory, based on the phenol employed.

Example 4

Preparation of 2-(2,4-di-tert-butylphenoxy)caproic acid

The procedure was as in Example 1. Instead of the addition of water, however, 240 g of 25% strength NaOH were added at 90° C. and the mixture was boiled under reflux for 5 hours. After separation of the phases, initial distillation was carried out up to an overhead temperature of 100° C. in order to distil off any residual alcohols. The mixture was acidified with 300 g of 18% strength HCl and washed neutral at 90° C. To remove residual water, a vacuum of down to 20 mbar was applied and the mixture was stirred at 90° C. for 1 hour. 323 g of pale yellow coloured 2-(2,4-di-tert-butylphenoxy)caproic acid (contents according to HPLC: 1.1% of residual phenol, 98.5% of 2-(2,4-di-tert-butylphenoxy)caproic acid) resulted. This corresponds to a yield of 99% of theory, based on the phenol employed.

Example 5

Preparation of 2-(2,4-di-tert-butylphenoxy)capronyl chloride 200 g of thionylchloride were added at 80° C. to 160 g of the carboxylic acid prepared in Example 4 and the mixture was stirred for 8 hours. Excess thionylchloride was removed in vacuo. 163 g of the 96.5% pure acid chloride remained.

Example 6

Preparation of 2-(2,4-di-tert-butylphenoxy)caproic acid esters

The procedure was as in Example 1. The reaction was carried out at 105° to 110° C., instead of at 140° C. For complete distillation of the alcohol, it was carried out under 300 mbar.

348 g of a viscous yellow oil of the following composition (1.2% of ethylbromo-caproate, 0.8% of residual phenol, 73% of ethyl 2-(2,4-di-tert-butylphenoxy)caproate and 25% of methyl 2-(2,4-di-tert-butylphenoxy)caproate) were obtained. This corresponds to 99% of theory.

Example 7

Preparation of 2-(2,4-di-tert-pentylphenoxy)caproic acid esters

The reaction was carried out as in Example 1. Instead of 2,4-di-tert-butylphenol, 234 g (1 mol) of 2,4-di-tert-pentylphenol were employed.

375 g of an ester mixture of the following composition resulted: 0.7% of residual phenol, 1.7% of ethyl 2-bromocaproate, 69% of ethyl 2-(2,4-di-tert-pentylphenoxy)caproate, 27% of methyl 2-(2,4-di-tert-pentylphenoxy)caproate. This corresponds to 97% of theory.

The acid prepared from this mixture was 97.4% pure (melting point 67° C.).

Example 8

Preparation of 2-(2,4-di-tert-pentylphenoxy)butyric acid

The reaction was carried out analogously to Example 1. Instead of ethyl 2-bromocaproate, 210 g of ethyl 2-bromobutyrate were employed. 348 g of an ester mixture resulted. This was hydrolysed as described to give 320 g of 2-(2,4-di-tert-pentylphenoxy)butyric acid (melting point 89° C.; 96.8% pure with 1.2% of residual phenol; 97% of theory).

Example 9

Preparation of 2-(2,4-di-pentylphenoxy)acetic acid

96% pure acid (melting point 115° to 120° C.; 1.8% of residual phenol) was prepared in an analogous manner in a yield of 95.6% of theory from chloroacetic acid and 2,4-di-tert-pentylphenol.

Example 10

Preparation of 2-(2-t-butyl-4-tert-pentylphenoxy) acetic acid 97.8% pure acid (melting point 140° to 144° C., 1.6% of residual phenol) was prepared in an analogous manner in a yield of 96.8% of theory from 2-t-butyl-4-tert-pentylphenol.

Example 11

Preparation of 4-(4-tert-pentylphenoxy)-γ-butyric acid

94% pure acid (2.8% of residual phenol) was prepared in an analogous manner in a yield of 92.6% of theory from γ-chlorobutyric acid and 4-tert-pentylphenol.

Example 12

Preparation of 4-tert-butylphenoxyacetic acid

94% pure acid (melting point 93° to 95° C., 1.4% of residual phenol) was prepared in an analogous manner in a yield of 93.8% of theory from 4-tert-butylphenol and methylchloroacetate.

Example 13

Preparation of 2-(3-tert-butyl-4-hydroxyphenoxy) myristic acid

92% pure acid (3.1% of residual hydroquinone) were obtained in a manner analogous to Example 1 in a yield of 91% of theory from 2-tert-butylhydroquinone and ethyl α-bromomyristate.

Example 14

Preparation of 2-(2-chloro-4-cyclohexyl)myristic acid 93.4% pure acid was obtained in an analogous manner to Example I in a yield of 92% of theory. Residual content of 1.05% of 2-chloro-4-cyclohexylphenol, from 2-chloro-4-cyclohexylphenol and ethyl α-bromomyristate.

We claim:

1. A process for the preparation of alkyl aryl ethers containing carboxyl groups or derivatives thereof by reaction of aromatic alcohols with alkyl halides containing carboxyl groups or derivatives thereof and basic alkali metal or alkaline earth metal compounds, wherein the reaction is carried out in the melt of the aromatic alcohol.

2. The process according to claim 1, wherein as the aromatic alcohol substituted or unsubstituted phenols or naphthols are used.

3. The process according to claim 1, wherein the basic alkali metal or alkaline earth metal compound is capable of reacting with aromatic alcohols to form an aromatic alcoholate and water or an aliphatic $C_1$–$C_4$-alcohol.

4. The process according to claim 1, wherein NaOH, $Na_2CO_3$, $K_2CO_3$, $Li_2CO_3$, $NaHCO_3$, LiOH, KOH or $KHCO_3$ or an aliphatic alkali metal $C_1$–$C_4$-alcoholcate of Na, Li or K is used as the basic alkali metal or alkaline earth metal compound.

5. The process according to claim 3, wherein the water formed during the formation of the aromatic alcoholate or the alcohol formed is removed during the reaction together with the solvent or suspending agent used, where appropriate, for the basic alkali metal or alkaline earth metal compound.

6. The process according to claim 1, wherein the alkyl halide containing carboxyl groups or derivatives thereof is added to the melt of the aromatic alcohol entirely before, partly before or simultaneously with the alkali metal or alkaline earth metal compound.

7. The process according to claim 1 for the preparation of alkyl aryl ethers containing carboxyl groups, of the formula (I)

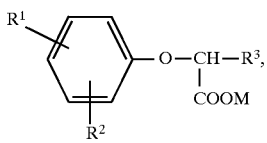

wherein the reaction is carried out employing phenols of the formula (II)

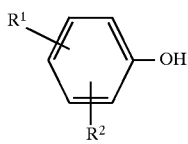

and alkyl halides containing carboxyl groups, of the formula (III)

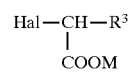

in the presence of basic alkali metal or alkaline earth metal compounds, wherein $R^1$ and $R^2$ independently of one another represent hydrogen, straight-chain or branched $C_1$–$C_8$-alkyl, $C_5$–$C_8$-cyclohexyl, $C_6$–$C_{10}$-aryl-$C_1$–$C_4$-alkyl, $C_6$–$C_{10}$-aryl, hydroxyl, $C_1$–$C_4$-alkoxy, $C_6$–$C_{10}$-aryloxy or halogen, $R^3$ represents hydrogen, straight-chain or branched $C_1$–$C_8$-alkyl, $C_5$–$C_8$cycloalkyl, $C_6$–$C_{10}$-aryl-$C_1$–$C_8$-alkyl, or COOM, M denotes Na, Li, K or $C_1$–$C_4$-alkyl and Hal represents Cl, Br, F or I.

8. The process according to claim 1, wherein 2-tert-butylphenol, 4-tert-butylphenol, 2,4-di-tert-butylphenol, 2-tert-pentylphenol, 4-tert-pentylphenol, 2,4-di-tert-pentylphenol, 2-tert-hexylphenol, 4-tert-hexylphenol, 2,4-di-tert-hexylphenol, 2-chloro-4-tert-amyl-phenol or 2-tert-butyl-hydroquinone is used as the aromatic alcohol and methyl chloroacetate, ethyl chloroacetate, methyl bromoacetate, ethyl α-bromopropionate, ethyl β-bromopropionate, ethyl α-bromobutyrate, ethyl α-bromoisobutyrate, ethyl γ-bromobutyrate or ethyl α-bromoisobutyrate is used as the alkyl halide containing carboxyl groups or derivatives thereof.

9. A process for the preparation of color film couplers wherein alkyl aryl ethers prepared by reacting an aromatic alcohol with an alkyl halide containing carboxyl groups or a derivative thereof and a basic alkali metal or alkaline earth metal compound, wherein the reaction is carried out in the melt of said aromatic alcohol are applied.

10. A process for the preparation of an acid chloride of an alkyl aryl ether containing carboxyl groups or derivatives thereof, said alkyl aryl ether being itself Prepared by reacting an aromatic alcohol with an alkyl halide containing carboxyl groups or a derivative thereof and a basic alkali metal or alkaline earth metal compound, wherein the reaction Is carried out in the melt of said aromatic alcohol, which comprises reacting said alkyl aryl ether or derivative thereof with thionyl chloride, $COCl_2$ or other chlorinating agent.

11. An intermediate for the preparation of plant protection agents or pharmaceuticals which comprises an alkyl aryl ether prepared by reacting an aromatic alcohol with an alkyl halide containing carboxyl groups or a derivative thereof and a basic alkali metal or alkaline earth metal compound, wherein the reaction is carried out in the melt of said aromatic alcohol.

* * * * *

UNITED STATES PATENT AND TRADEMARK OFFICE
CERTIFICATE OF CORRECTION

PATENT NO. : 5,869,735
DATED : February 9, 1999
INVENTOR(S): Antons, et al.

It is certified that error appears in the above-identified patent and that said Letters Patent is hereby corrected as shown below:

| | |
|---|---|
| Col. 7, claim 1 line 1 | Delete " the preparation of alkly aryl ethers " and substitute -- the preparation of an alkyl aryl ether -- |
| Col. 7, claim 1 line 2 | Delete " derivatives " and substitute -- a derivative -- |
| Col. 7, claim 1 line 3 | Delete " of aromatic alcohols with alkyl halides " and substitute -- an aromatic alcohol with an alkyl halide -- |
| Col. 7, claim 1 line 4 | Delete " derivatives thereof and basic " and substitute -- a derivative thereof and a basic -- |
| Col. 7, claim 1 line 5 | Delete " compounds " and substitute -- compound -- |
| Col. 7, claim 1 line 6 | Delete " the " (second occurrence) and substitute -- said -- |

UNITED STATES PATENT AND TRADEMARK OFFICE
CERTIFICATE OF CORRECTION

PATENT NO. : 5,869,735
DATED : February 9, 1999
INVENTOR(S) : Antons, et al.

It is certified that error appears in the above-identified patent and that said Letters Patent is hereby corrected as shown below:

Col. 7, line 27  Delete " $C_1$-$C_4$-alcoholcate " and substitute -- $C_1$-$C_4$-alcoholate --

Signed and Sealed this

Twenty-fifth Day of April, 2000

Q. TODD DICKINSON

Attest:

Attesting Officer

Director of Patents and Trademarks